(12) United States Patent
Pah

(10) Patent No.: US 7,727,254 B2
(45) Date of Patent: Jun. 1, 2010

(54) METHOD OF REMOVING HEART VALVE STENOSIS

(76) Inventor: Gunnar M. Pah, Wehrbachweg 8/6, Kirchberg in Tirol (AT) 6365

( * ) Notice: Subject to any disclaimer, the term of this patent is extended or adjusted under 35 U.S.C. 154(b) by 0 days.

(21) Appl. No.: 12/275,420

(22) Filed: Nov. 21, 2008

(65) Prior Publication Data
US 2009/0069841 A1    Mar. 12, 2009

Related U.S. Application Data

(63) Continuation of application No. PCT/EP2007/054777, filed on May 16, 2007.

(30) Foreign Application Priority Data
May 23, 2006   (DE)   ........................ 10 2006 024 176

(51) Int. Cl.
*A61M 29/02* (2006.01)
*A61F 2/00* (2006.01)
(52) U.S. Cl. ...................................................... 606/200
(58) Field of Classification Search ................. 606/194, 606/200
See application file for complete search history.

(56) References Cited

U.S. PATENT DOCUMENTS

| | | | |
|---|---|---|---|
| 5,295,958 A * | 3/1994 | Shturman | 604/103.07 |
| 5,941,896 A | 8/1999 | Kerr | |
| 5,954,745 A | 9/1999 | Gertler et al. | |
| 6,029,671 A | 2/2000 | Stevens et al. | |
| 6,485,500 B1 * | 11/2002 | Kokish et al. | 606/194 |
| 6,632,236 B2 * | 10/2003 | Hogendijk | 606/198 |
| 6,645,224 B2 | 11/2003 | Gilson et al. | |
| 6,692,512 B2 | 2/2004 | Jang | |
| 6,746,463 B1 | 6/2004 | Schwartz | |
| 6,761,732 B2 | 7/2004 | Burkett et al. | |

(Continued)

FOREIGN PATENT DOCUMENTS

WO    99/23976 A1    5/1999

(Continued)

OTHER PUBLICATIONS

International Search Report dated Dec. 13, 2007, from PCT/EP2007/054777, filed May 16, 2007.

*Primary Examiner*—Anhtuan T Nguyen
*Assistant Examiner*—Ryan J Severson
(74) *Attorney, Agent, or Firm*—Houston Eliseeva LLP

(57) ABSTRACT

The invention relates to a device and a method for the removal of a heart valve stenosis, in which a filter catheter is arranged in a vessel section located downstream of the heart valve, and a valvuplasty catheter is arranged in the area of the heart valve. The filter catheter has in one embodiment of the invention at its distal end a radial filter which is unfolded radially until it fits up against the vessel wall. The catheter lumen is closed in such a way that blood must flow through the filter. After the filter has been unfolded, the valvuplasty catheter is inflated in the area of the heart valve to remove the heart valve stenosis, while debris and plaque which are released are collected in the filter. In an alternative membrane, the filter catheter may be sealed relative to the vessel wall by means of a sealing element, while an external filter is connected to the filter catheter to filter debris and plaque from the blood.

14 Claims, 2 Drawing Sheets

U.S. PATENT DOCUMENTS

| | | |
|---|---|---|
| 6,896,690 B1 * | 5/2005 | Lambrecht et al. .......... 606/200 |
| 6,951,570 B2 | 10/2005 | Linder et al. |
| 6,962,598 B2 | 11/2005 | Linder et al. |
| 6,964,673 B2 | 11/2005 | Tsugita et al. |
| 7,108,707 B2 | 9/2006 | Huter et al. |
| 7,166,120 B2 | 1/2007 | Kusleika |
| 7,229,462 B2 | 6/2007 | Sutton et al. |
| 7,229,464 B2 | 6/2007 | Hanson et al. |
| 7,241,305 B2 | 7/2007 | Ladd |
| 7,252,675 B2 | 8/2007 | Denison et al. |
| 7,322,957 B2 | 1/2008 | Kletschka et al. |
| 7,338,510 B2 | 3/2008 | Boylan et al. |
| 7,371,249 B2 | 5/2008 | Douk et al. |
| 7,374,561 B2 | 5/2008 | Barbut |
| 7,410,491 B2 | 8/2008 | Hopkins et al. |
| 7,425,215 B2 | 9/2008 | Boyle et al. |
| 2001/0044591 A1 | 11/2001 | Stevens et al. |
| 2002/0022859 A1 | 2/2002 | Hogendijk |
| 2002/0026212 A1 | 2/2002 | Wholey et al. |
| 2002/0077596 A1 | 6/2002 | McKenzie et al. |
| 2005/0004594 A1 | 1/2005 | Nool et al. |
| 2005/0075662 A1 * | 4/2005 | Pedersen et al. ............ 606/194 |
| 2005/0228432 A1 | 10/2005 | Hogendijk et al. |
| 2006/0074484 A1 | 4/2006 | Huber |
| 2006/0100553 A1 | 5/2006 | Lodin |
| 2006/0100658 A1 | 5/2006 | Obana et al. |
| 2006/0106417 A1 | 5/2006 | Tessmer et al. |
| 2006/0173490 A1 | 8/2006 | Lafontaine et al. |
| 2008/0140003 A1 | 6/2008 | Bei et al. |

FOREIGN PATENT DOCUMENTS

| | | |
|---|---|---|
| WO | 00/67668 A1 | 11/2000 |
| WO | 01/91844 A1 | 12/2001 |
| WO | 03/089041 A1 | 10/2003 |
| WO | 2004/026175 A1 | 4/2004 |

\* cited by examiner

US 7,727,254 B2

METHOD OF REMOVING HEART VALVE STENOSIS

RELATED APPLICATIONS

This application is a Continuation of PCT Application No. PCT/EP2007/054777 filed on May 16, 2007 which claims priority to German Patent Application Number DE 10 2006 024 176.2, filed on May 23, 2006, both of which are incorporated herein by reference in their entirety.

BACKGROUND OF THE INVENTION

The heart pumps oxygen-rich blood into the arteries. When the heart beats, blood is supplied first to the aorta, and an aortic valve is located between the left ventricle and the aorta. This aortic valve opens and closes to control the direction of blood flow. It is open in particular during the systolic heartbeat to allow blood to flow into the aorta. During the diastolic heartbeats the aortic valve is closed, to prevent the return flow of blood into the heart. For various reasons, however, the aortic valve may be damaged and stenosed. If this occurs, the aortic valve does not open to its normal extent, and the blood flow from the heart into the aorta is impeded. This leads to a condition described as aortic valve stenosis.

Known from U.S. Pat. No. 6,746,463 B1 are a device and a method for the removal of such an aortic valve stenosis, in which a balloon catheter with a guide wire is arranged with the balloon in the area of the aortic valve. The balloon catheter is then inflated. The balloon catheter has cutting blades which are braced radially during inflation. The cutting edges of each blade cut into the aortic valve and remove any stenosis which has formed on the aortic valve.

Known from WO 03/089041 A1 is a device for minimally-invasive intravascular or intravasal aortic valve extraction within the aorta of a human heart. This device is intended to improve the minimally-invasive intravasal extraction of the aortic valve, with complete exclusion of the risk of embolism due to tissue and/or calcium particles which may enter the blood circulation system. It should moreover be possible for the surgeon to remove diseased areas of the heart valve individually, locally and selectively, and this preferably under direct visual observation of the diseased areas of the heart valve. For this purpose the device is in the form of a perfusion catheter which provides at least one perfusion passage and at least two dilation units spaced apart over the length of the catheter in the proximal catheter zone. The perfusion passage passes through both dilation units which in the inflated state form a seal, at least virtually fluid-tight, with a vessel wall, preferably the aorta wall. At least the distal side dilation unit should be provided with at least one through passage, through which at least one auxiliary catheter for aortic valve open blocking may be passed with fluid-tightness, and/or the perfusion catheter provided at least one operating passage with an exit opening in the area between two dilation units, through which the auxiliary catheter or catheters may be passed for the aortic valve open blocking. By means of the perfusion catheter, which substantially encompasses a hollow passage, a flow of blood should be ensured through the hollow passage, so that the surgical intervention is made on the beating heart, without impairing the heart's activity. The two dilation units are inflated on the heart side and the aorta side, bounding the aortic valve between them, and forming a fluid-tight seal with the respective vessel wall. Operations on the aortic valve are conducted in the operating space bounded by the two dilation units and the hollow passage, via separate access to the operating space.

A synthetic aortic valve is known e.g. from EP 1 335 683 B1. Other implantable heart valve prostheses, together with catheters for the implantation of such heart valve prostheses, are disclosed by EP 592 410 B1, US 2004/0210304 A1, U.S. Pat. No. 7,018,406 B2, WO2006/127765 A1, US 2003/0036795 A1, U.S. Pat. No. 5,411,552, U.S. Pat. No. 6,168,614 B1, U.S. Pat. No. 6,582,462 B1 and WO91/17720.

From WO 99/23976 it is known that in the removal of a stenosis, for example using a balloon catheter, the material causing the stenosis is dissolved, flows away with the arterial blood and, if it is large enough, may close a blood vessel and possibly cause a heart attack. For this purpose it is said to be known that filters may be placed in human blood vessels, to trap such embolism-causing material. It is also said to be known that removable filters may be used for this purpose. Such removable filters usually involve a filter of the umbrella type which has a filter membrane located on a folding frame on a guide wire. With this device it is said to be a drawback that, on folding together of the filter, the material which causes an embolism tends to be pressed outwards and re-enters the bloodstream.

Known from WO 0067688 is a further filter element with a folding filter body, which may be moved between a folded position for movement through a vascular system and an unfolded position to extend in a blood vessel so that blood flowing through the blood vessel is guided through the filter element. A distal inlet zone of the filter body has one or more inlet openings which are so dimensioned that blood and embolism-causing material are able to enter the filter body, and a proximal outlet zone with a multiplicity of outlet openings which are so dimensioned that blood may pass through but embolism-causing material is retained. The filter body is at least partly a laminate structure with a membrane provided with a bio-compatible coating. The thickness of the coating is 4 to 40% of the thickness of the membrane.

U.S. Pat. No. 6,676,683 B1 discloses a filter catheter which has at its end section an extending and expanding filter. The catheter itself is a guide wire along which further catheters, which encompass this guide wire, may be guided for suitable positioning in the blood vessels.

EP 980 278 B1 discloses a similar catheter with a guide wire, at the end of which an expandable filter element is provided.

SUMMARY OF THE INVENTION

To avoid problems associated with conventional approaches, it is proposed to use a protective device against embolisms which comprises a collapsible filter element mounted on a filter carrier, for advancing through the blood vessel system of a patient. Here the filter element may be moved between a folded storage position in the filter carrier for movement through the vascular system, and an unfolded position in which a blood vessel is blocked off so that the blood guided through the blood vessel is instead guided through the filter element. Here the filter element comprises a collapsible filter body with an inlet end and an outlet end, wherein the inlet end of the filter body has one or more openings allowing blood and embolism-causing material to enter the filter body, and the outlet end has a multiplicity of outlet openings which are so dimensioned that blood is able to pass through them but undesired embolism-causing material is retained within the filter body, and means are provided for closing the inlet end and the outlet end of the filter body. These openings are closed before the filter is closed for its removal. This publication proposes for this purpose a multiplicity of different filter elements.

The invention is based on the problem of creating a device for the filtering of blood during removal of a heart valve stenosis in which, with a valvuplasty of the heart valve, stenosis material flowing away is reliably held back, and which permits a minimally-invasive, intravasal valvuplasty of a heart valve which may be performed simply, quickly and safely.

The invention relates to a device for the filtering of blood during removal of a heart valve stenosis and a method of removing a heart valve stenosis.

In general, according to one aspect, the invention features, device for the filtering of blood during removal of a heart valve stenosis comprising a filter catheter which has at its distal end, for filtering the blood to be found downstream behind a heart valve, a filter which may be pushed distally into and out of the filter catheter, wherein the filter is designed to expand radially in such a way that in the extended state the filter fits up against a blood vessel wall, and the filter catheter has a catheter lumen which is so designed that a further catheter may be guided through the catheter lumen.

A further problem of the invention is to create a method for the removal of a heart valve stenosis which may be conducted safely. In this method, stenosis material flowing away is reliably held back, and the method may be carried out simply, quickly and safely.

Thus, in general, according to another aspect, the invention features, a method of removing a heart valve stenosis, wherein a filter catheter is inserted and arranged in a vessel section downstream of the heart valve and against the direction of flow of the blood, wherein the filter catheter has at its distal end a radial filter which is radially infolded until it fits up against the vessel wall and the catheter lumen is closed in such a way that blood must flow through the filter, and a balloon catheter is inserted and arranged in the area of the heart valve through an open catheter lumen of the filter catheter, and after the unfolding of the filter a balloon of the balloon catheter is inflated in the area of the heart valve to remove the heart valve stenosis, while debris and plaque which are released are collected in the filter.

In the method according to the invention, a filter catheter and a balloon valvuplasty catheter are used. The filter catheter is arranged a short distance downstream of the heart valve. The filter catheter has either a filter element between the filter catheter and the blood vessel or a seal unit, and can then be connected to an external filter. The filter catheter has an open catheter lumen, through which the balloon catheter is inserted and through which if necessary bloodflow is diverted outwards. With the balloon catheter, firstly a valvuplasty balloon is placed in the area of the heart valve. The valvuplasty balloon is guided through the heart valve by means of a guide wire. The balloon is then inflated, which forces open the native heart valve. In some examples, this inflation is performed to remove a stenosis and to destroy the native valve with the balloon catheter. The native valve is thereafter replaced with an artificial valve.

Since this process bursts deposits (plaque and/or debris) away, the blood which passes during the performing of a valvuplasty is filtered. This is done mainly by the filter provided on the filter catheter located downstream of the heart valve.

In a further advantageous embodiment, this filter catheter is sealed radially relative to the blood vessel, so that the blood flows out through the filter catheter and is guided through a heart-lung machine in which a filter is provided, or through another external filter.

The filter catheter may be inserted in the body by all known means of access, and guided to the heart valve via the descending aorta (aorta), the aortic arch and the ascending aorta. For example the filter catheter may be inserted/introduced through the femoral artery. The filter catheter is so designed that it may be inserted into the aorta against the direction of the bloodflow. In the extended state the filter is roughly funnel-shaped, becoming wider towards the distal end. This ensures that, when the filter is withdrawn into the filter catheter, the plaque and debris which are collected at the filter are tunneled into the catheter lumen and do not remain in the aorta.

The filter catheter is a long tube with a one-way valve at the proximal end, provided for inserting the balloon/valvuplasty catheter. The balloon/valvuplasty catheter is inserted through this one-way valve. When the balloon catheter is removed, the valve closes automatically, so that any leakage/escape of blood is prevented.

At the other end, which is furthest away from the operator of the filter catheter, namely the distal end, is where the filter and/or seal unit are mounted. The filter is made preferably of a fabric, but may also be made of all other possible known filter media. A fabric filter is provided with a ring and axial struts of a so-called "memory material". Such a memory material may be obtained commercially for example under the brand name "nitinol". Any other memory material is of course also possible. Because of the memory material, the filter is able to expand into a funnel shape as it extends out of the catheter, to fit with its radial periphery against the inner wall of the blood vessel. Since the lumen, i.e. the hollow space of the catheter, is blocked by the valve, the blood flows into the intermediate space between the outer body of the catheter and the blood vessel. At the same time the blood is filtered, with plaque and debris being restrained in the folding filter. When the filter is retracted, the plaque and debris are withdrawn with the catheter and removed from the body of the patient.

According to the invention, there are various possible mechanisms for extending the filter. The simplest mechanism according to the invention provides for the filter catheter to be made up of two coaxial tubular bodies, with the inner body connected securely to the filter. By sliding the inner body inside the outer body, the filter is pushed in and out of the outer body.

In a further advantageous embodiment, the filter is pushed out of the catheter or back into it by a wire or similar device. It is also conceivable to provide a spring element, which acts in a similar manner.

The diameter of the hollow body or lumen is 7 to 20 French (F)—"French" is a unit of size commonly used for catheters.

The filter may be extended up to a maximum diameter of 50 mm.

In a further advantageous embodiment, the catheter is sealed in the blood vessel and a femoral bypass is fitted, with a heart-lung machine connected to the bypass to filter the blood. Here the sealing may be affected in different ways, for example by an element similar in design to the filter, but impervious to fluids. The filter catheter may also be sealed relative to the blood vessel by a balloon encompassing, and in the inflated state surrounding, the distal end of the catheter. Such a device according to the invention may also be advantageous when a lot of plaque and debris occurs that external filtering is necessary.

Preferably the filter or sealing element is arranged between the aortic valve and the inlets (Ostie) to the coronary arteries. By this means the risk of an infarct during such a procedure is advantageously reduced. The filter or sealing element may also be fitted in the direction of flow after the coronary arteries, in the ascending aorta.

In the placing of a femoral bypass, a filter catheter is used which has a Y bifurcation at its proximal end. In this case one end of the Y bifurcation outlets/inlets are provided with a one-way valve, and the other end have a cap which may be released for the connection of the heart-lung machine. In contrast to the prior art, the filter element according to the invention is located downstream of a heart valve on which a valvuplasty is to be performed, while the filter—in contrast to the prior art—is fitted around the radial periphery.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
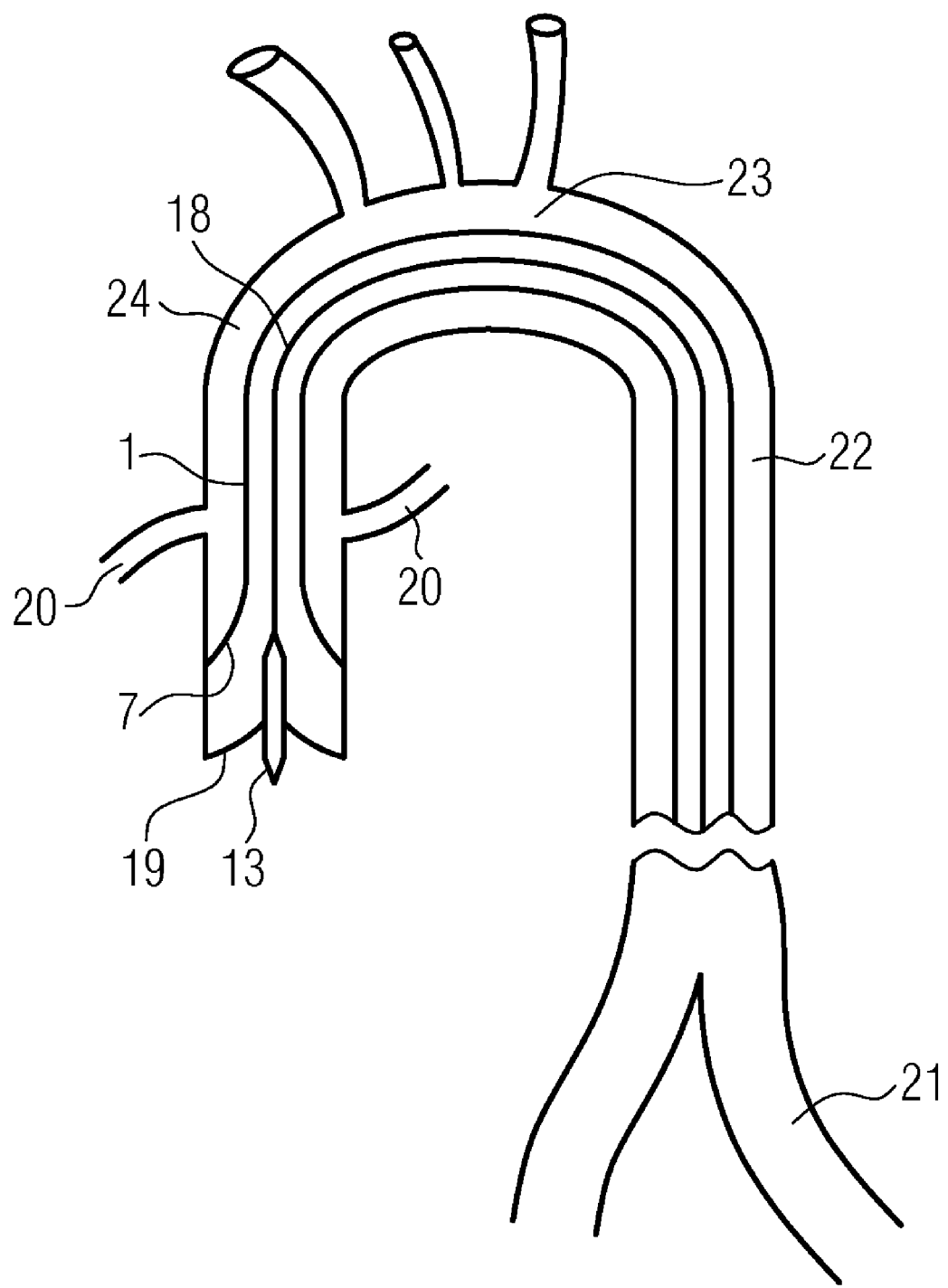
FIG. 1 a highly schematic view of the point of installation position of the filter according to the invention, and FIG. 2 a highly schematic view of the catheter according to the invention.

The device 1 according to the invention is a catheter 1 with an outer body 2 and an inner body 3. The outer body 2 terminates with a distal end 4, while at the distal end 4 the inner body 3, at the distal end of which the filter 5 is provided, may be pushed out.

The outer body 2 and the inner body 3 are for example substantially hollow-cylindrical or tubular in form.

The filter 5 is made of a filter fabric which is provided with a ring 6 and axial struts 7 of a memory material. The filter fabric is stretched between the struts 7.

In the state in which they are inserted in the body, the ring 6, the struts 7 and the filter material therefore lie within the outer catheter body 2 and are pressed by distal pushing of the inner body 3 into a blood vessel 8, so that the ring 6 fits up against the blood vessel 8 with sealing from the inside. Blood flowing in the proximal direction of the arrows 9 flows through the filter 5 and arrives in the space 10 bounded by the outer catheter body 2 and the blood vessel 8. The catheter lumen 11 has a diameter of 7 to 20 French and is sealed at its proximal end by an one-way valve 12. In a preferred embodiment, the catheter lumen 11 has a diameter of approximately 4 to 7 millimeters. Through the valve 12 and the catheter inner body 3, a balloon catheter 13 may be inserted from the proximal to the distal end. The balloon provided at the distal end of the balloon/valvuplasty catheter may be inflated in the area of the aortic valve.

The maximum distal diameter of the filter comes to around 35 mm to 50 mm.

The filter catheter 1 may also be made of a single-piece hollow cylindrical or tubular body, instead of an outer and an inner body. In the wall of the former body there are hollow passages running from the proximal to the distal end, in each of which it is mounted a metal wire, provided that there is a recess at the distal end of this body to accommodate the filter. On its proximal side the filter is fixed to a ring, which in turn is located at the end of the metal wires. The metal wires may therefore be used to advance the filter out of the catheter body and to withdraw it. The metal wires are all moved simultaneously, to avoid tilting of the filter in the catheter. Preferably around three to five guide wires are provided spaced apart from one another at the same angle in the catheter body.

Figure 2:
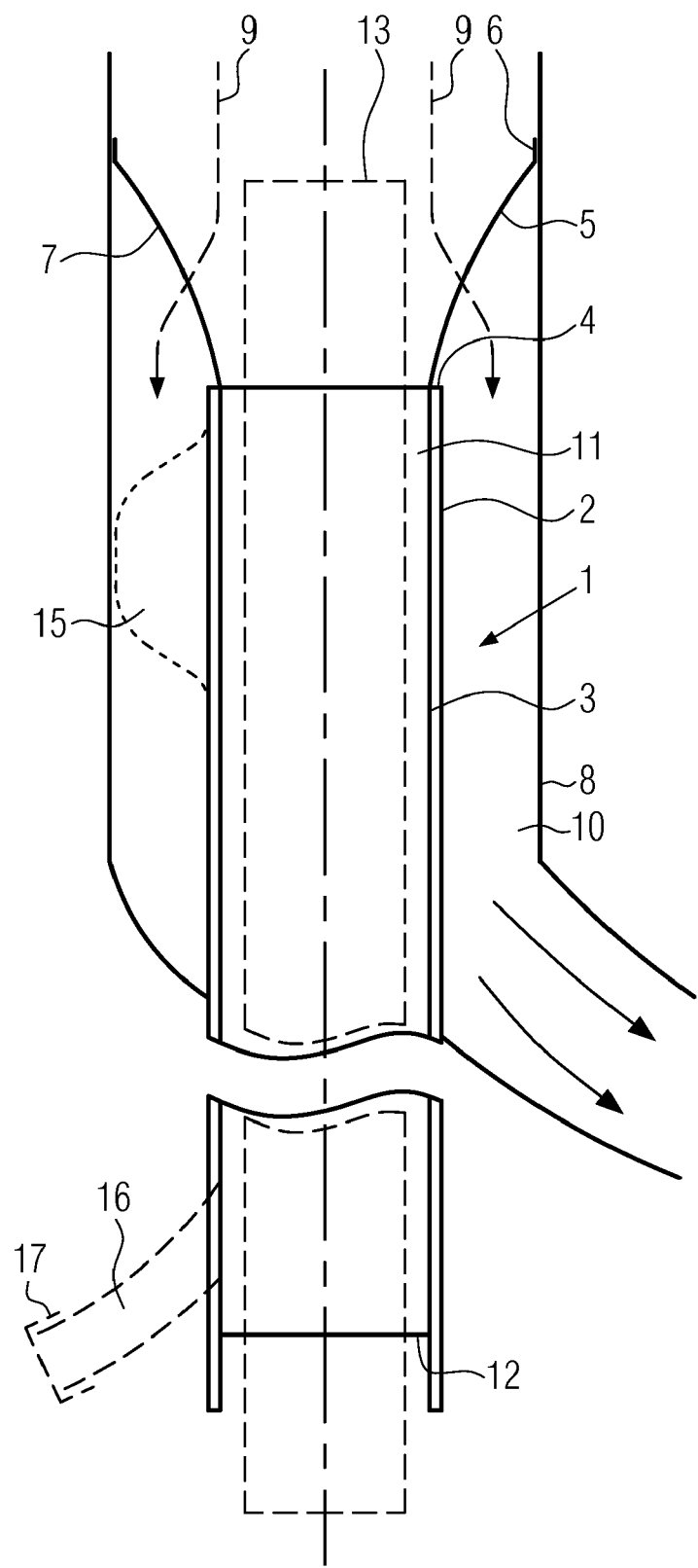

The body of the filter 5 shown in FIG. 2 is curved somewhat convex relative to the heart valve. Other shapes are however also usable, such as e.g. concave curved forms, in particular a parabolic concave curved form.

In a further advantageous embodiment, the device 1 may have on the catheter outer body 2 an inflatable seal/balloon 15 which, in contrast to the illustration in FIG. 2, runs all around the distal end of the outer catheter body 2 in such a way that the blood vessel 8 is sealed outside the catheter body 2. In this embodiment the catheter 2 has a separate bifurcation 16, preferably before the valve 12, and where applicable sealed by a cap 17. The bifurcation 16 makes it possible for blood to be withdrawn from the blood vessel 8 through the lumen 11, and for example fed to an external heart-lung machine with an external filter.

Preferably the device 1 according to the invention is provided with both an inflatable balloon seal 15 and also the filter 5. If the filter is so greatly clogged by plaque and debris that the blood flow in the blood vessel 8 behind the filter 5 is no longer adequate, the device 15 may be inflated and the filter 5 simultaneously drawn into the catheter outer body 2, while at the same time the blood is taken from the lumen 11 of the catheter via the bifurcation 16 and fed to a heart-lung machine with an external filter. In connection with this, the valve 12 is tightly closed. Here it is advantageous that by means of the connection to the heart-lung machine, plaque and debris is also safely sucked up when the filter 5 is retracted into the main body 2, and is not introduced into the rest of the vascular system of the human body.

The balloon/valvuplasty catheter 13 is inserted for example by means of a guide wire 18 through the catheter lumen 11, and expanded in the area of the aortic valve 19. The filter 7 or device 1 is preferably so arranged that it is located in the ascending aorta 24 and preferably before the coronary aorta 20 and after the aortic valve 19 (FIG. 1).

As depicted in FIG. 1, the catheters are inserted via the femoral arteries 21, the descending aorta 22, the aortic arch 23 and the ascending aorta 24. The catheters 1, 13 are thus inserted against the direction of the blood flow and are positioned with their distal ends in the area of the heart valve or adjacent to the area of the heart valve.

The device 1 may of course also be introduced through any other known access and not exclusively via the femoral aorta.

In the case of the device according to the invention it is of advantage that, due to the provision of a filter element at the distal end of a hollow catheter with lumen, wherein the filter comprises a self-unfolding supporting framework made of a memory material, simple and quick fitting of the filter is possible.

Through the alternative or simultaneous provision of an inflatable device at the distal end of the catheter, the blood may also be filtered externally, instead of being filtered through the filter. This may also take place successively, or to assist in removal of the filter without the release of plaque.

The catheter lumen of the filter catheter has, preferably over its entire length, a constant diameter. It may therefore be expedient to make the outside diameter of the catheter in the distal end section somewhat greater than in the remainder of the catheter, so that there is adequate space to accommodate the filter. The remaining area of the filter catheter can not be of any desired thickness, since it needs a certain flexibility for introduction into the curved aorta. This flexibility is not always available with the catheter materials normally used, if a diameter of much more than 15 French (5 mm) is exceeded.

In the method according to the invention it is advantageous that the repair of an aortic valve caused by a stenosis may be carried out quickly and safely, in particular without risk of embolism/stroke.

The invention may be summarized as follows:

The invention relates to a device and a method for the removal of a heart valve stenosis, in which a filter catheter is located in a vessel section downstream of the heart valve, and a balloon catheter is positioned in an area of the heart valve. The filter catheter has in one embodiment of the invention, at its distal end, a radial filter which is radially unfolded until it fits up against the vessel wall. The catheter lumen is closed in such a way that blood must flow through the filter. After unfolding of the filter, the balloon catheter is inflated in the area of the heart valve to remove the heart valve stenosis, while debris and plaque which are released are collected in the filter. In an alternative embodiment the filter catheter may be sealed against the vessel wall by means of a sealing element, while an external filter is connected to the filter catheter, in order to filter debris and plaque from the blood.

In operation, after collecting the debris and plaque in the filter, the filter is drawn into the filter catheter and then the filter catheter is removed. Usually, the balloon catheter is removed first and then the filter catheter, although the balloon catheter can be removed simultaneously with the filter catheter. Regarding the seal unit, the filter is retracted into the filter catheter before inflating the seal element and after retraction of the filter, blood is carried away through the lumen of the filter catheter, after which the seal element is deflated and the filter catheter is removed

LIST OF REFERENCE NUMBERS 1 filter catheter
2 outer body
3 inner body
4 distal end
5 filter
6 ring
7 axial struts
8 blood vessel
9 arrows
10 space
11 lumen
12 valve
13 balloon catheter
15 inflatable seal
16 bifurcation
17 cap
18 guide wire
19 aortic valve
20 coronary aorta
21 femoral arteries
22 descending aorta
23 aortic arch
24 ascending aorta While this invention has been particularly shown and described with references to preferred embodiments thereof, it will be understood by those skilled in the art that various changes in form and details may be made therein without departing from the scope of the invention encompassed by the appended claims.

What is claimed is:

1. A method of removing a heart valve stenosis, comprising:
    inserting and then positioning a filter catheter in a vessel section downstream of a heart valve and against the direction of flow of the blood, wherein the filter catheter has at its distal end a radial filter;
    pushing the radial filter out of the filter catheter and radially unfolding the radial filter to fit against the vessel wall and closing a catheter lumen of the filter catheter to direct blood through the filter, the catheter lumen being closed with a valve located at a proximal end of the filter catheter;
    inserting and positioning a balloon catheter in the area of the heart valve through the catheter lumen and the valve of the filter catheter; and
    after the unfolding of the filter, inflating a balloon of the balloon catheter in an area of the heart valve to remove the heart valve stenosis, while collecting released debris and plaque with the filter;
    wherein the catheter lumen has a diameter of approximately 4 to 7 millimeters (mm).

2. A method of removing a heart valve stenosis, comprising:
    inserting and then positioning a filter catheter in a vessel section downstream of a heart valve and against the direction of flow of the blood, wherein the filter catheter has at its distal end a radial filter;
    pushing the radial filter out of the filter catheter and radially unfolding the radial filter to fit against the vessel wall and closing a catheter lumen of the filter catheter to direct blood through the filter;
    inserting and positioning a balloon catheter in the area of the heart valve through an open catheter lumen of the filter catheter; and
    after the unfolding of the filter, inflating a balloon of the balloon catheter in an area of the heart valve to remove the heart valve stenosis, while collecting released debris and plaque with the filter.

3. A method according to claim 2, wherein, in the extended state, the filter is funnel-shaped, with the filter expanding towards the distal end.

4. A method according to claim 2, wherein the filter catheter has a greater circumference at a distal end section, in which the filter is stored, than over the rest of its length, the diameter of the catheter lumen being constant over a length of the filter catheter.

5. A method according to claim 2, wherein the filter has a supporting framework made of a memory material, comprising a ring which, after pushing out, fits up against the wall of the blood vessel.

6. A method according to claim 5, wherein the supporting framework comprises axial struts of memory material.

7. A method according to claim 2, wherein in the extended state the filter has a roughly parabolic convex or concave shape.

8. A method according to claim 2, further comprising, after collecting the debris and plaque in the filter, drawing the filter into the filter catheter and then removing the filter catheter.

9. A method according to claim 8, further comprising firstly removing the balloon catheter and then the filter catheter.

10. A method according to claim 8, further comprising simultaneously removing the balloon catheter and the filter catheter.

11. A method according to claim 8, further comprising using a seal unit at the distal end of the filter catheter to seal space between the filter catheter and a blood vessel wall to direct blood to flow through the catheter lumen.

12. A method according to claim 11, further comprising feeding blood from the catheter lumen to a heart-lung machine with an external filter.

13. A method according to claim 11, further comprising inflating an inflatable seal element of the seal unit at the distal end of the filter catheter.

14. A method of removing a heart valve stenosis, comprising:

- inserting and then positioning a filter catheter in a vessel section downstream of a heart valve and against the direction of flow of the blood, wherein the filter catheter has at its distal end a radial filter;
- radially unfolding the radial filter to fit against the vessel wall and closing a catheter lumen of the filter catheter to direct blood through the filter;
- inserting and positioning a balloon catheter in the area of the heart valve through an open catheter lumen of the filter catheter;
- after the unfolding of the filter, inflating a balloon of the balloon catheter in an area of the heart valve to remove the heart valve stenosis, while collecting released debris and plaque with the filter;
- after collecting the debris and plaque in the filter, drawing the filter into the filter catheter and then removing the filter catheter;
- using a seal unit at the distal end of the filter catheter to seal space between the filter catheter and a blood vessel wall to direct blood to flow through the catheter lumen;
- before the filter is retracted into the filter catheter, inflating the seal element, and
- after retraction of the filter, blood is carried away through the catheter lumen of the filter catheter, after which the seal element is deflated and the filter catheter is removed.

* * * * *